United States Patent [19]
Suzuki

[11] Patent Number: 5,247,318
[45] Date of Patent: Sep. 21, 1993

[54] FUNDUS CAMERA FOR PHOTOGRAPHY USING A FLUORESCENT AGENT

[75] Inventor: Haruhiko Suzuki, Tokyo, Japan
[73] Assignee: Kabushiki Kaisha Topcon, Tokyo, Japan
[21] Appl. No.: 804,560
[22] Filed: Dec. 10, 1991
[30] Foreign Application Priority Data
  Dec. 11, 1990 [JP] Japan ................................. 2-401380
[51] Int. Cl.⁵ .............................................. A61B 3/10
[52] U.S. Cl. .................................... 351/213; 351/206; 351/207; 354/62; 250/458.1
[58] Field of Search ............... 351/206, 205, 207, 208, 351/213; 354/62; 250/458.1, 459.1, 461.1, 461.2

[56] References Cited
U.S. PATENT DOCUMENTS
4,452,517 6/1984 Kobayakawa ....................... 354/62
4,690,525 9/1987 Kobayashi et al. ................. 351/206
4,799,783 1/1989 Takahashi et al. .................. 351/206

Primary Examiner—Bruce Y. Arnold
Assistant Examiner—Hung Xuan Dang
Attorney, Agent, or Firm—Finnegan, Henderson, Farabow, Garrett & Dunner

[57] ABSTRACT

The fundus camera of this invention for taking photographs by fluorescence comprises an exciter filter 7 in an illuminating optical system 1, and a barrier filter 16 in a photographic optical system 2. A member 11 for eliminating harmful reflected light from an objective lens 13 is also provided in the illuminating optical system 1. This member 11 for eliminating harmful reflected light comprises dark spots 21, 22, which transmit light below a lower wavelength limit, and cut out light above the lower wavelength limit, of the barrier filter 16.

4 Claims, 2 Drawing Sheets

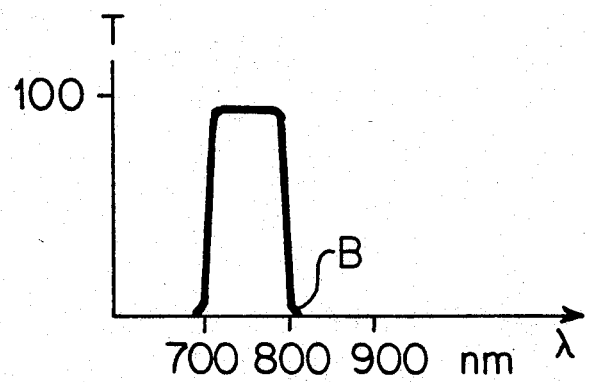
FIG. 2
FIG. 3
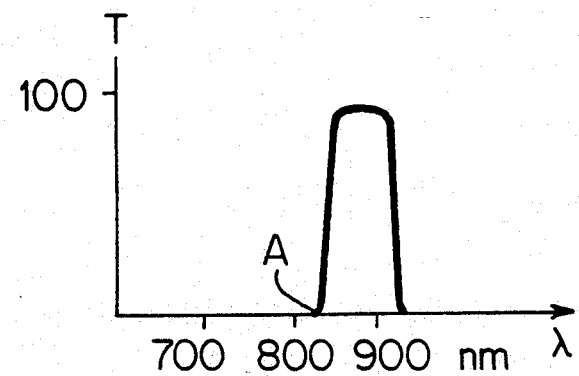
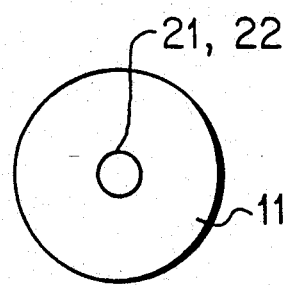
FIG. 4
FIG. 5
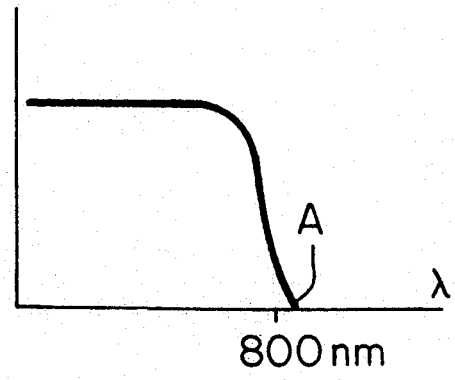

FUNDUS CAMERA FOR PHOTOGRAPHY USING A FLUORESCENT AGENT

BACKGROUND OF THE INVENTION

1. Field of the Invention

This invention concerns the improvement of a fundus camera which takes photographs by means of a fluorescent agent, and which can eliminate harmful reflected light.

2. Description of the Prior Art

A fundus camera is known in the art which takes photographs by means of a fluorescent agent. This fundus camera comprises an exciter filter in the illuminating optical system, and a barrier filter is also provided in the photographic optical system. The fundus is illuminated by illuminating light in a specific wavelength range in the illuminating light that has passed through the exciter filter. A fluorescent agent flowing in the blood vessels of the fundus is excited by this illuminating light in a specific wavelength range, and emits fluorescence. The fluorescence from the fundus passes through the barrier filter to be guided to a film or other recording means, and an image of the fundus is thereby recorded on the recording means.

A plate having a black spot in its center is interposed in the optical path of the illuminating optical system so as to eliminate harmful reflected light from the surface of the objective lens. If there were no black spot, part of the illuminating light reflected from the surface of the objective lens would pass through the aperture diaphragm of the photographic optical system so as to reach the film or other recording means. In other words, illuminating light reflected from the surface of the objective lens, which is harmful reflected light, would reach the recording means and lead to deterioration of the image of the fundus photographed by fluorescence. If such a black spot is provided, the illuminating light which is the cause of this harmful reflected light is prevented from reaching the objective lens. Further, an image of the black spot is formed at the position of the aperture diaphragm of the photographic optical system.

However, in this conventional fundus camera which takes photographs using a fluorescent agent, the black spot is interposed in the illuminating optical system. Part of the illuminating light is therefore cut off by the black spot, and a dark shadow of the spot appears in the center region of the fundus image which is undesirable.

SUMMARY OF THE INVENTION

It is therefore an object of this invention to provide a fundus camera using a fluorescent agent wherein harmful reflected light from the objective lens can be eliminated without casting a shadow in the center region of the fundus when it is illuminated.

To resolve the above problem, the fundus camera for taking photographs using a fluorescent agent according to this invention having an exciter filter placed in the illuminating optical path and a barrier filter placed in the photographic optical path, is characterized in that a member for eliminating harmful reflected light from the objective lens is placed in the illuminating optical system, and that this member comprises a dark spot which transmits wavelengths below a lower wavelength limit of the barrier filter, and cuts out wavelengths above the lower wavelength limit of same.

In the fundus camera for taking photographs using a fluorescent agent according to this invention, illuminating light for exciting the fluorescent agent which has passed through the exciter filter, passes through the objective lens without being stopped by the member for eliminating harmful reflected light to illuminate the fundus. The formation of a shadow in the center region of the fundus due to this member is therefore prevented.

Part of the illuminating light for exciting the fluorescent agent which has passed through the member for eliminating harmful reflected light, is reflected by the surface of the objective lens for exciting the fluorescent agent. This illuminating light, which has been reflected by the surface of the objective lens and has passed through the aperture diaphragm, is however cut out by the barrier filter of the photographic optical system.

A small amount of illuminating light having a wavelength which does not contribute to excitation of the fluorescent agent and which can pass through the barrier filter, is transmitted by the exciter filter and proceeds to the objective lens. However, of the small amount of light of wavelengths above the lower limit of the barrier filter, light which would otherwise proceed towards the aperture diaphragm of the photographic optical system and be reflected by objective lens to become harmful reflected light if there were no dark spot, is cut out when there is such a spot. This small amount of harmful reflected light is therefore prevented from reaching the film.

BRIEF DESCRIPTION OF THE DRAWINGS

FIG. 2 is a wavelength characteristic diagram of the exciter filter shown in FIG. 1.

FIG. 3 is a wavelength characteristic diagram of the barrier filter shown in FIG. 1 according to this invention.

FIG. 4 is a plan view of the member for eliminating harmful reflected light shown in FIG. 1.

FIG. 5 is a wavelength transmission characteristic diagram of the dark spots.

DESCRIPTION OF THE PREFERRED EMBODIMENT

Figure 1:
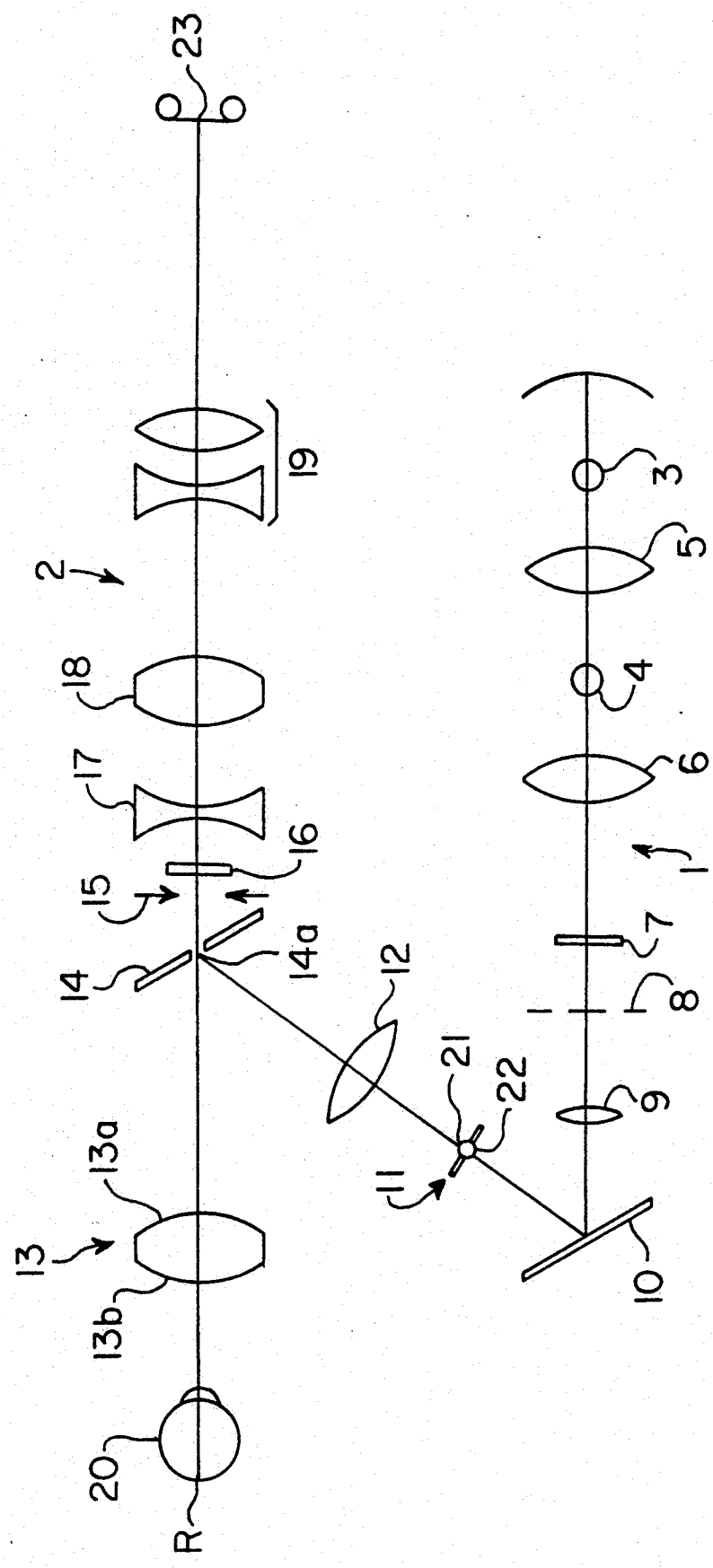
FIG. 1 is an optical drawing of a fundus camera for taking photographs using a fluorescent agent according to this invention.

In FIG. 1, 1 is an illuminating optical system and 2 is a photographic optical system. The illuminating optical system 1 comprises a halogen lamp 3, xenon lamp 4, condensing lens 5, condensing lens 16, exciter filter 7, annular diaphragm 8, relay lens 9, reflecting mirror 10, harmful reflected light eliminating member 11 and relay lens 12.

The photographic optical system 2 comprises an objective lens 13, holed mirror 14, aperture diaphragm 15, barrier filter 16, focusing lens 17, magnifying lens 18 and imaging lens 19. The objective lens 13 faces a subject's eye 20.

The halogen lamp 3 and xenon lamp 4 are in mutually conjugate positions with respect to the condensing lens 5. As shown in FIG. 2, the exciter filter 7 has characteristics which transmit illuminating light from a wavelength of approximately 700 nm to approximately 800 nm. The fluorescent agent is excited by illuminating light of a wavelength of approximately 700 nm to approximately 800 nm.

As shown in FIG. 3, the barrier filter 16 has wavelength characteristics which transmit infrared light-excited fluorescence of a wavelength from approximately 800 nm to approximately 920 nm. Herein, the lower wavelength limit A of light transmitted by this barrier filter 16 is approximately 815 nm.

The exciter filter 7 transmits a small amount of light of higher wavelength than the lower wavelength limit A of the barrier filter 16. In FIG. 2, the symbol B denotes the wavelength region of this small amount of illuminating light. Illuminating light which has passed through the exciter filter 7 contains a small amount of illuminating light of wavelength above the lower limit A of the barrier filter 16. Thus the small amount of illuminating light does not contribute to excitation of the fluorescent agent. This illuminating light passes via the annular diaphragm 8 and relay lens 9, is reflected by the reflecting mirror 10, and is guided to the member 11 for eliminating harmful reflected light. As shown in FIG. 4, this member 11 has a disc shape, and dark spots 21, 22 are formed in its center. These dark spots 21, 22 are formed on both sides of the member 11.

The dark spot 21 eliminates harmful light which would be reflected by the first surface 13a, and the dark spot 22 eliminates harmful light which would be reflected by the second surface 13b, of the objective lens 13. As shown in FIG. 5, the transmission characteristics of the dark spots 21, 22 are such as to cut out light of wavelengths above the lower wavelength limit A, and transmit light of wavelengths below the lower wavelength limit A, of the barrier filter 16.

The illuminating light for exciting the fluorescent agent is transmitted via the member for eliminating harmful reflected light 11 including the dark spots 21, 22, and thence via the relay lens 12, holed mirror 14 and objective lens 13 so as to illuminate the fundus R of the subject's eye 20. Shadows due to the dark spots 21, 22 are thereby prevented from appearing in the center region of the fundus R. Of the small amount of illuminating light of wavelengths above the lower wavelength limit A of the barrier filter 16, illuminating light which would be reflected by the first surface 13a and second surface 13b of the objective lens 13, and which would become harmful reflected illumination, is cut out by these dark spots 21, 22.

Fluorescence from the fundus due to the illuminating light which is guided to the holed mirror 14 via the objective lens 13, passes via the hole 14a and the aperture diaphragm 15 to reach the barrier filter 16. It is then transmitted via the barrier filter 16 and the focusing lens 17, magnifying lens 18 and imaging lens 19 so as to reach the film 23 where an image of the fundus photographed by fluorescence is formed.

Illuminating light reflected from the fundus R, and light which is reflected from the first surface 13a and the second surface 13b of the objective lens 13, is also transmitted via the hole 14a of the holed mirror 14 and the aperture diaphragm 15 to reach the barrier filter 16. The further passage of this reflected light is however prevented by the barrier filter 16.

This invention is not only adaptable to the above-mentioned fundus camera for taking photographs by infra-red illuminating light, but also adaptable to a fundus camera for taking photographs by visible illumination light, since we can produce harmful reflected light eliminating member 11 for visible illuminating light.

What is claimed is:

1. A fundus camera for taking photographs using a fluorescent agent, the camera comprising:
   an illuminating optical system;
   a photographic optical system;
   an objective lens facing an eye of a subject, the objective lens being located in the photographic optical system;
   an exciter filter located in the illuminating optical system for transmitting illuminating light with wavelengths within a certain range to excite the fluorescent agent;
   a barrier filter located in the photographic optical system for transmitting fluorescence excited by the illuminating light, the barrier filter having a lower wavelength limit;
   a member located in the illuminating optical system for transmitting the illuminating light with wavelengths below the lower wavelength limit, and for cutting out the illuminating light with wavelengths above the lower wavelength limit, so that the illuminating light reflected by the objective lens is cut out by the barrier filter.

2. The fundus camera according to claim 1, wherein said member has a first dark spot for eliminating harmful reflected light from a first surface of the objective lens, and a second dark spot for eliminating harmful reflected light from a second surface of the objective lens.

3. The fundus camera according to claim 2, wherein the first and second dark spots are located on opposite sides of the member.

4. A fundus camera for taking photographs using a fluorescent agent, the camera comprising:
   an illuminating optical system;
   a photographic optical system;
   an objective lens facing a patient's eye, the objective lens being located in the photographic optical system;
   an exciter filter located in the illuminating optical system for transmitting illuminating light with wavelengths within a certain range to excite the fluorescent agent;
   a barrier filter located in the photographic optical system for transmitting fluorescence excited by the illuminating light, the barrier filter having a lower wavelength limit, the illuminating light including a small amount of light with wavelengths higher than said lower wavelength limit;
   a member located in the illuminating optical system for cutting out said small amount of light, and for transmitting the illuminating light with wavelengths below the lower wavelength limit, so that the illuminating light reflected by the objective lens is cut out by the barrier filter.

* * * * *